United States Patent
Zhou et al.

(10) Patent No.: US 7,036,585 B2
(45) Date of Patent: May 2, 2006

(54) AQUEOUS VISCOELASTIC FLUID

(75) Inventors: Jian Zhou, Sugar Land, TX (US); Trevor Hughes, Cambridge (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 218 days.

(21) Appl. No.: 10/250,417

(22) PCT Filed: Feb. 13, 2002

(86) PCT No.: PCT/GB02/00589

§ 371 (c)(1), (2), (4) Date: Dec. 12, 2003

(87) PCT Pub. No.: WO02/064946

PCT Pub. Date: Aug. 22, 2002

(65) Prior Publication Data

US 2004/0221989 A1    Nov. 11, 2004

(30) Foreign Application Priority Data

Feb. 13, 2001    (GB) .................................... 0103449

(51) Int. Cl.
*E21B 43/22*    (2006.01)

(52) U.S. Cl. .................... 166/268; 166/270.1; 166/403; 507/239

(58) Field of Classification Search ................ 166/268, 166/270.1, 403; 507/239
See application file for complete search history.

(56) References Cited

U.S. PATENT DOCUMENTS

| | | | |
|---|---|---|---|
| 5,258,137 A | 11/1993 | Bonekamp et al. | |
| 5,551,516 A | 9/1996 | Norman et al. | |
| 5,964,295 A | 10/1999 | Brown et al. | |
| 5,979,557 A | 11/1999 | Card et al. | |
| 6,306,800 B1 | 10/2001 | Samuel et al. | |
| 6,412,561 B1 | 7/2002 | Brown et al. | |
| 6,435,277 B1 | 8/2002 | Qu et al. | |
| 6,881,709 B1 * | 4/2005 | Nelson et al. | 507/203 |
| 6,908,888 B1 * | 6/2005 | Lee et al. | 507/219 |
| 6,920,928 B1 * | 7/2005 | Davies et al. | 166/279 |
| 2002/0004464 A1 | 1/2002 | Nelson et al. | |

FOREIGN PATENT DOCUMENTS

| | | |
|---|---|---|
| EP | 0 835 983 A2 | 4/1998 |
| EP | 0 835 983 A3 | 4/1998 |

(Continued)

OTHER PUBLICATIONS

Butler et al, The hydrolysis of acetic anhydride. Part VII. Catalysis by pyridine and methylpyridines in acetate buffers, Journal of the Chem. Society, 1961, pp. 4362-4367.

(Continued)

*Primary Examiner*—Frank S. Tsay
(74) *Attorney, Agent, or Firm*—Jody Lynn DeStefanis; William L. Wang; Dale Gaudier

(57) ABSTRACT

The invention concerns an aqueous viscoelastic fluid for use in the recovery of hydrocarbons. According to the invention this fluid comprises a first viscoelastic surfactant and a second surfactant able to decompose under downhole conditions to release a compound itself able to reduce the viscosity of the aqueous viscoelastic fluid.

21 Claims, 10 Drawing Sheets

FOREIGN PATENT DOCUMENTS

| | | |
|---|---|---|
| GB | 2 334 277 A | 8/1999 |
| WO | 94/09852 A1 | 5/1994 |
| WO | 98/56497 A1 | 12/1998 |
| WO | 01/18147 A1 | 3/2001 |
| WO | 01/77487 A2 | 10/2001 |
| WO | 01/77487 A3 | 10/2001 |

OTHER PUBLICATIONS

Fersht et al, The acetylpyridinium ion intermediate in pyridine-catalyzed hydrolysis and acyl transfer reactions of acetic anhydride. Observation, kinetics, structure-reactivity correlations, and effects of concentrated salt solutions, Journal of the American Chemical Society, vol. 92, 1970, pp. 5432-5442.

Holmberg, Cleavable surfactants, Novel Surfactants (Holmberg ed.), Marcel Dekker Inc, New York, 1998, pp. 333-358.

Kaiser et al, Synthesis of esters of acid-unstable alcohols by means of $n$-butyllithium, Journal of Organic Chemistry, vol. 35, No. 4, 1970, pp. 1198-1199.

Kivinen, Mechanisms of substitution at the COX group, The Chemistry of Acyl Halides (Patai ed.), Interscience Publishers, New York, 1972, pp. 177-230.

Krüger et al, Esterquats, Novel Surfactants (Holmberg ed.), Marcel Dekker Inc, New York, 1998, pp. 115-138.

Satchell, An outline of acylation, Quarterly Reviews of the Chem. Society, vol. 17, 1963, pp. 160-203.

Smith et al, Aliphatic nucleophilic substitution, March's Advanced Organic Chemistry, 5$^{th}$ edition, Wiley-Interscience, New York, 2001, pp. 498-502, 506-514, 574-578.

Smith et al, Aromatic electrophilic substitution, March's Advanced Organic Chemistry, 5$^{th}$ edition, Wiley-Interscience, New York, 2001, pp. 701-704.

Sommer et al, Alkylation of amines. A general exhaustive alkylation method for the synthesis of quaternary ammonium compounds, Journal of Organic Chemistry, vol. 36, No. 6, 1971, pp. 824-828.

Sommer et al, Alkylation of amines. A new method for the synthesis of quaternary ammonium compounds from primary and secondary amines, Journal of Organic Chemistry, vol. 35, 1970, pp. 1558-1562.

Yoneda et al, A kinetic study of the reaction between sulfite ion and propylene oxide, Journal of Organic Chemistry, vol. 40, No. 3, 1975, pp. 375-377.

* cited by examiner

AQUEOUS VISCOELASTIC FLUID

The present invention concerns an aqueous viscoelastic fluid for use in the recovery of hydrocarbons and, in particular, for use as a fracturing fluid.

BACKGROUND OF THE INVENTION

Hydrocarbons such as oil or natural gas are obtained from hydrocarbon-bearing subterranean geologic formations via flow paths connecting a reservoir of said formations and the wellbore. Impeded flow paths may lead to an insufficient hydrocarbon production. In such case, various techniques are used to stimulate this production. Amongst these techniques, it is common to inject specialised fluids via the wellbore into the formation at sufficient pressures to create fractures in the formation rocks through which the hydrocarbons may more readily flow into the wellbore. The latter technique is referred to as fracturing or hydraulic fracturing and the specialised fluids used in said technique are referred to fracturing fluids.

Ideally, fracturing fluids should impart a minimal pressure drop in the pipe within the wellbore during placement and have an adequate viscosity to carry a propping agent that prevents the fracture from closing. Also, they should have a minimal leak-off rate and should degrade so as not to leave residual material that may prevent accurate hydrocarbons to flow back into the wellbore.

PRIOR ART

Aqueous fracturing fluids wherein the gelling agent is a viscoelastic surfactant have been developed and commercialised. They are disclosed notably in the patents published under the numbers U.S. Pat. No. 4,695,389, U.S. Pat. No. 4,725,372 and U.S. Pat. No. 5,551,516. An example of such fluid is commercialised by the company group Schlumberger™ under the trademark ClearFRAC™. It is a mixture of a quaternary ammonium salt, N-erucyl-N,N-bis(2-hydroxyethyl)-N-methyl ammonium chloride, with isopropanol and brine, said brine typically including water and either 3% by weight of ammonium chloride or 4% by weight of potassium chloride. In such fluids, surfactant molecules, present at a sufficient concentration, aggregate into overlapping worm- or rod-like micelles. This confers a sufficient viscoelasticity to said fluids for carrying the propping agent. At very high shear rate however, in particular above $170\ s^{-1}$, the viscosity falls drastically. This allows the fluid to be pumped down the wellbore. Also, the worm- or rod-like micelles aggregates tend to break by contact with hydrocarbons. So, if no surfactant emulsion is effectively formed, the surfactant molecules are normally carried along the fracture to the well bore during hydrocarbon backflow.

Under certain circumstances, for example when fracturing dry gas reservoirs wherein negligible quantities petroleum gas condense during production, the breaking of the gel can be hindered by the absence of any significant quantities of liquid hydrocarbon in the produced fluids. As a result, the efficiency with which the fracturing fluid is removed from the propped fracture is reduced.

That is one of the reasons why it has been proposed to add delayed breakers to viscoelastic fracturing fluids. These delayed breakers are able to break the fluid gel structure and reduce its viscosity at an appropriate time after the fracturing operation per se.

Delayed breakers of aqueous viscoelastic fluids comprising viscoelastic surfactant have been disclosed in the application published under the number WO-01/77487. They can be external or internal breakers.

External breakers are initially isolated from the surfactant molecules of the fluid. Typically, they consist of a solid material suspended and transported by this fluid as it creates the propped fracture. The solid material has generally a core-shell structure where the core is the chemical which breaks the gel and the shell is an encapsulating material which isolates the core from the gel. At an appropriate time within the propped fracture, the shell material dissolves, decomposes or ruptures and the core material breaks the gel.

Internal breakers are compounds which are initially dissolved within the fluid and are not isolated from the surfactant molecules. At an appropriate time, they decompose to release degradation products which break the gel. In the above-referenced application WO-01/77487, it is taught that the viscosity of an aqueous viscoelastic gel comprising viscoelastic surfactants consisting of long chain quaternary ammonium salts is reduced by the addition of esters. Esters have by themselves a little effect on the initial gel rheology. However, they can decompose to release alcohols that decrease the gel viscosity.

The gel breaking efficiency of alcohols increases with their concentration in the gel, the temperature and, also, with the molecular weight of said alcohols. However, the compatibility of esters with the viscoelastic surfactant based gel decreases with their hydrophobicity. As the molecular weight of alcohols is proportional to the hydrophobicity of the esters, then the ester approach is limited by the relationship between the hydrophobicity of the esters and their compatibility with the gel.

SUMMARY OF THE INVENTION

Considering the above prior art, one problem that the invention is proposing to solve is to carry out an aqueous viscoelastic fluid for use in the recovery of hydrocarbons and, in particular, for use as a fracturing fluid, said fracturing fluid comprising a compatible internal breaking system able to release efficient breaker compounds.

As a solution to the above problem, the invention concerns, in a first aspect, an aqueous viscoelastic fluid for use in the recovery of hydrocarbons, comprising: a first surfactant, said surfactant being viscoelastic; and a second surfactant, said second surfactant being able to decompose under downhole conditions to release a compound, said compound being able to reduce the viscosity of the aqueous viscoelastic fluid.

In a second aspect, the invention concerns a method for use in the recovery of hydrocarbons comprising the following steps: providing an aqueous viscoelastic fluid comprising a first surfactant, said surfactant being viscoelastic, and a second surfactant able to decompose under downhole conditions; allowing said second surfactant to decompose under downhole conditions to release a compound able to reduce the viscosity of the aqueous viscoelastic fluid; and allowing the viscosity of the fluid to be reduced downhole.

The second surfactant is, as the first surfactant, amphiphilic. It has a hydrophilic head group and a hydrophobic tail group. It is compatible with the first surfactant and may even participate in the formation of the viscoelastic gel. Under certain conditions or/and after a certain time, it decomposes to release degradation products, one of these degradation products being a compound able to reduce the viscosity of the viscoelastic gel and break this gel.

BRIEF DESCRIPTION OF THE DRAWINGS

The invention will be better understood in the light of the following description of non-limiting and illustrative embodiments given with reference to the accompanying drawings, in which:

the FIG. 1 shows the breakdown reaction of erucyl ester methylene dimethyl ethyl ammonium chloride;

Figure 2:
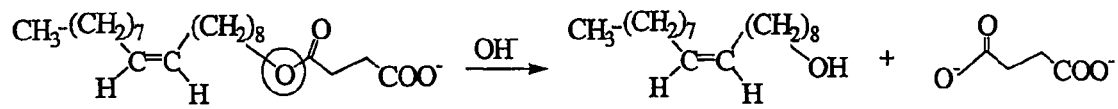
Figure 3:
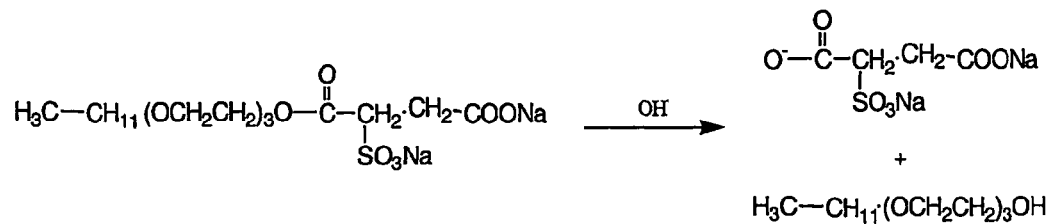
Figure 4:
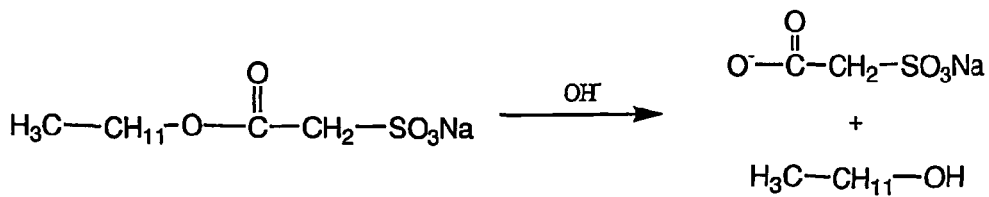
Figure 5:
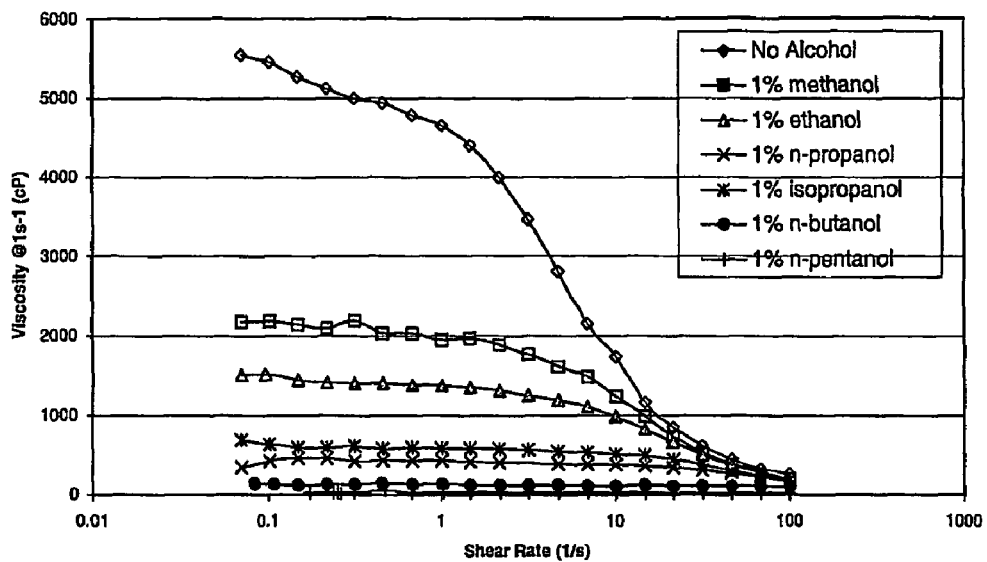
Figure 6:
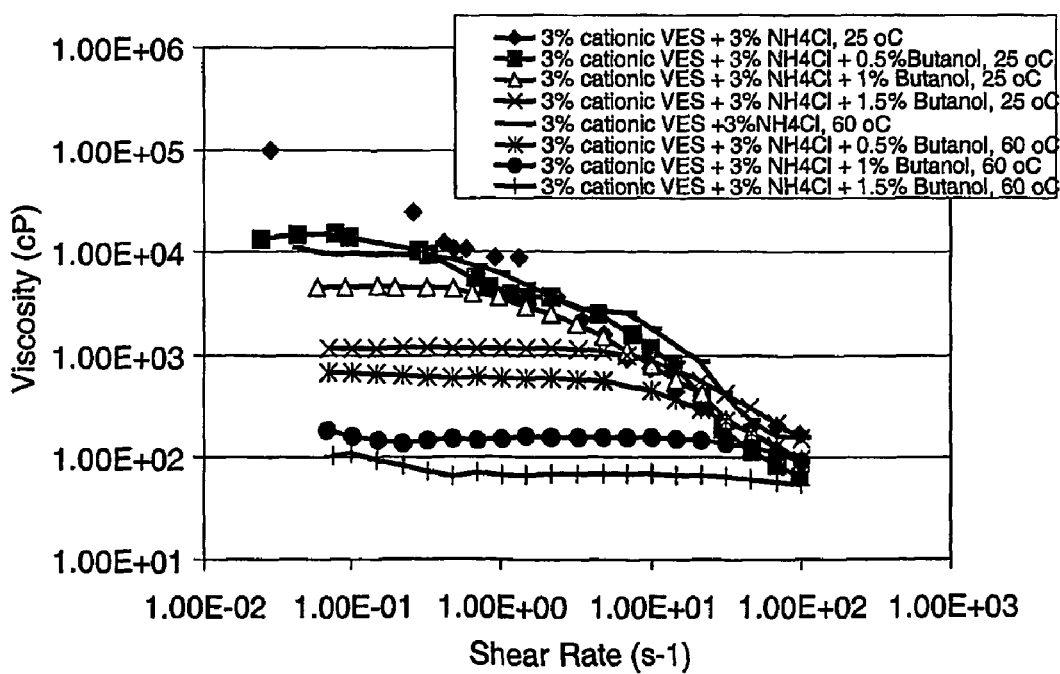
Figure 7:
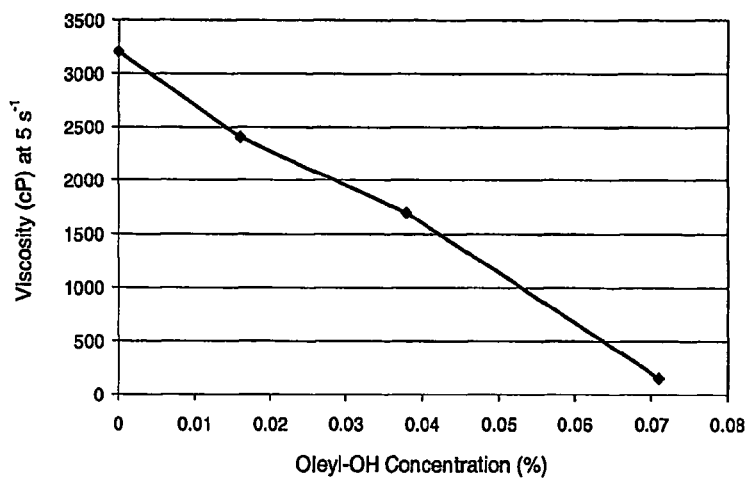
Figure 8:
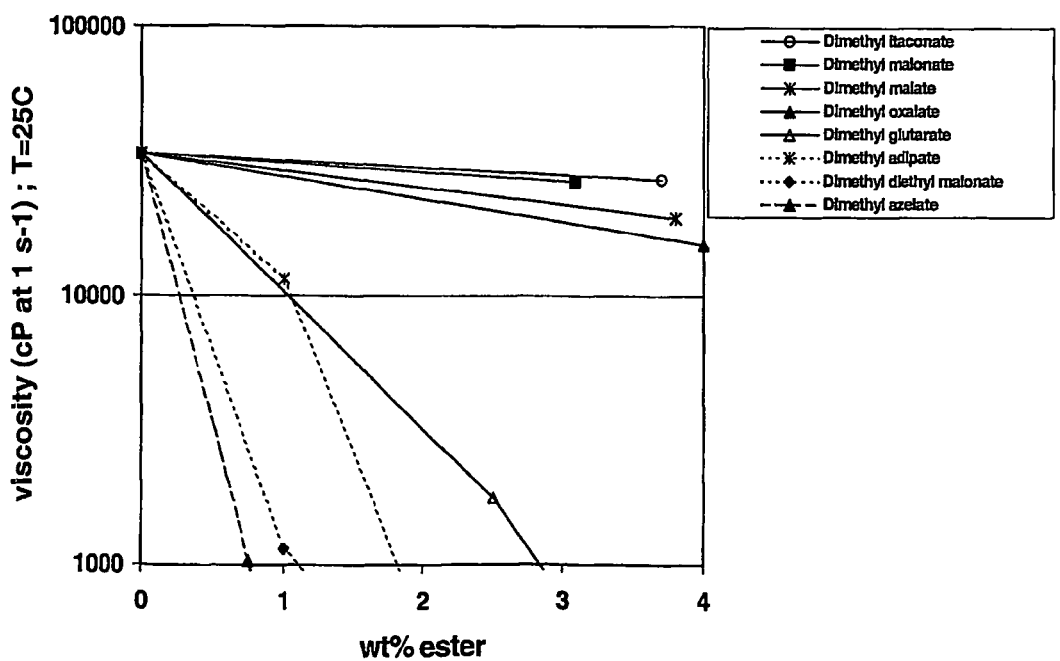
Figure 9:
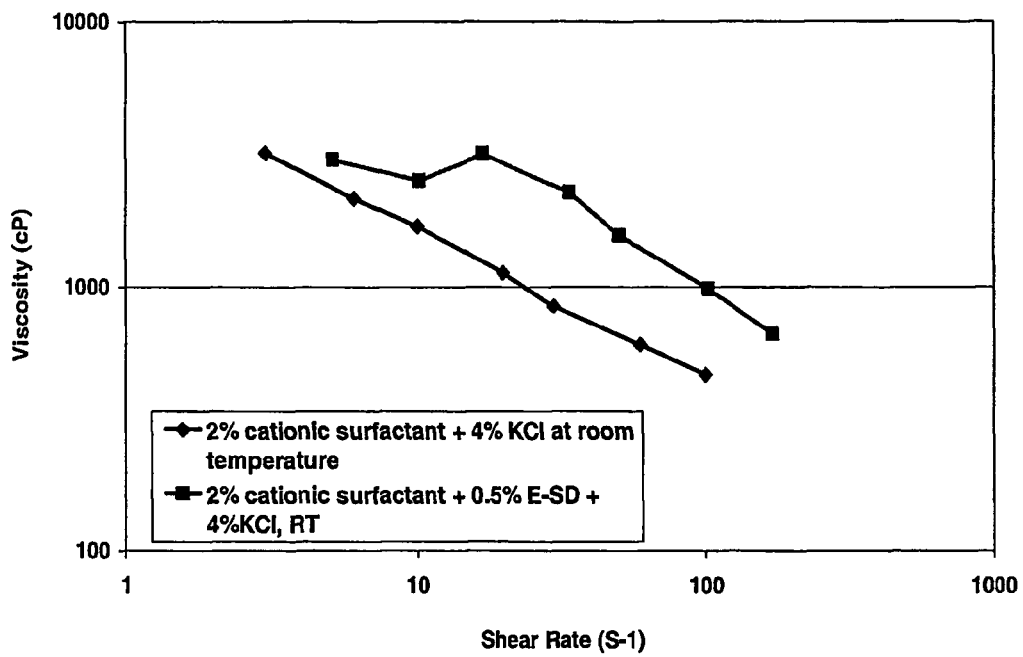
Figure 10:
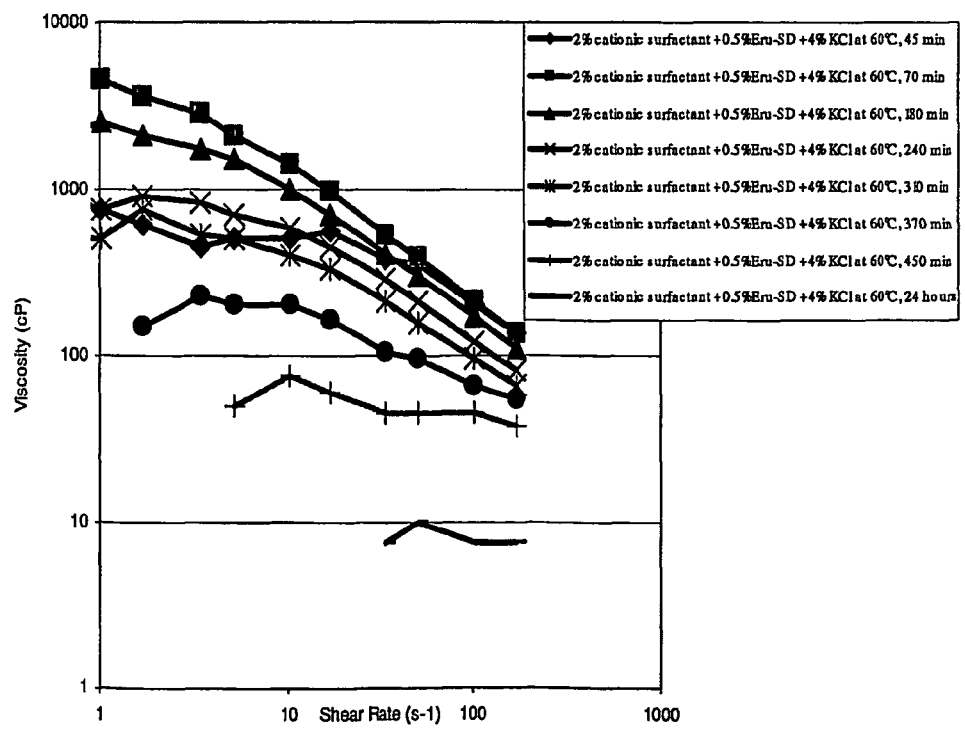
Figure 11:
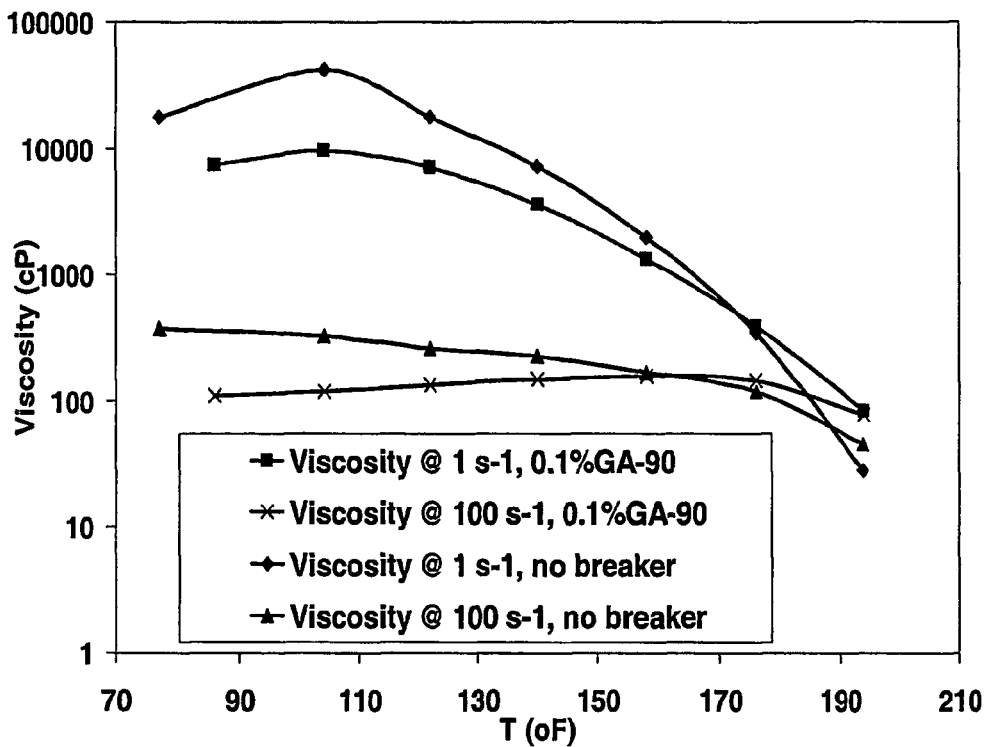
Figure 12:
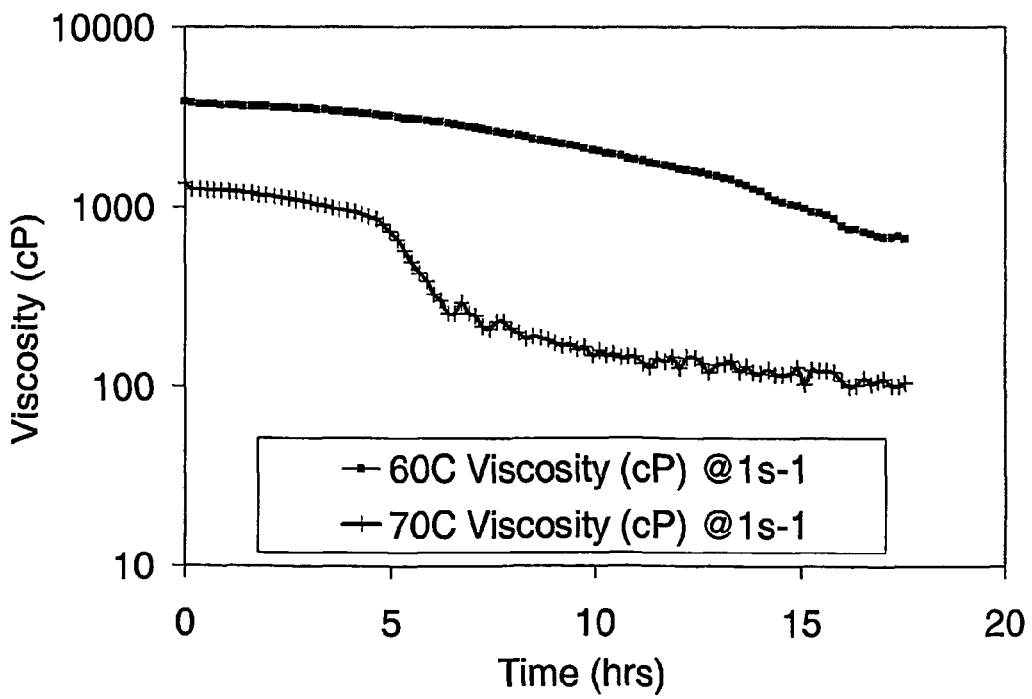
Figure 13:
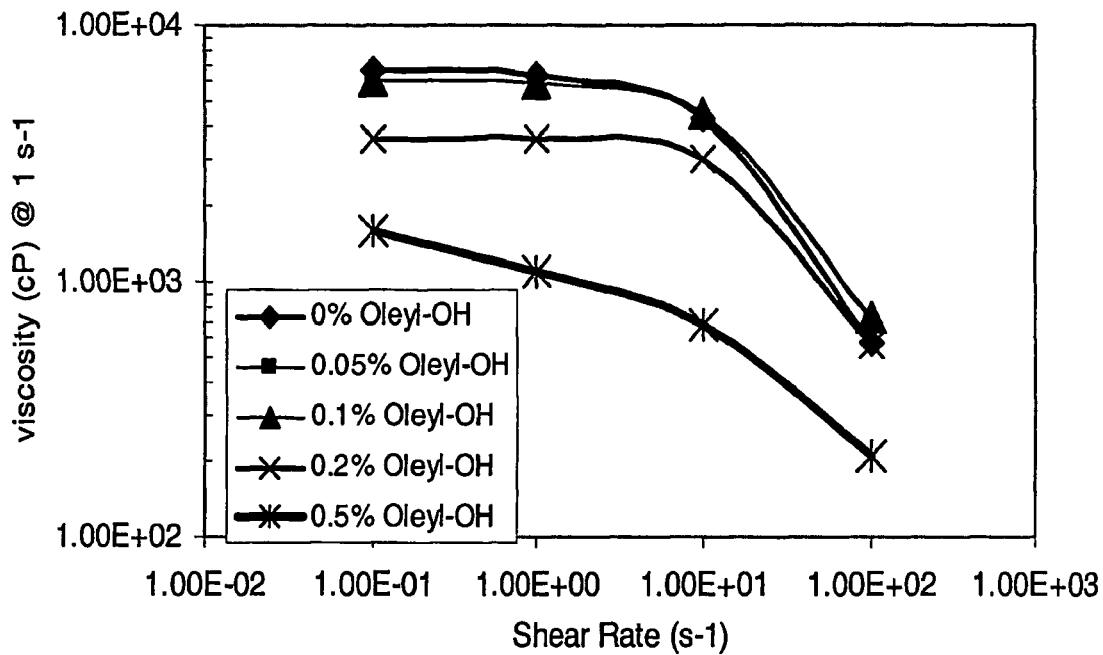
Figure 14:
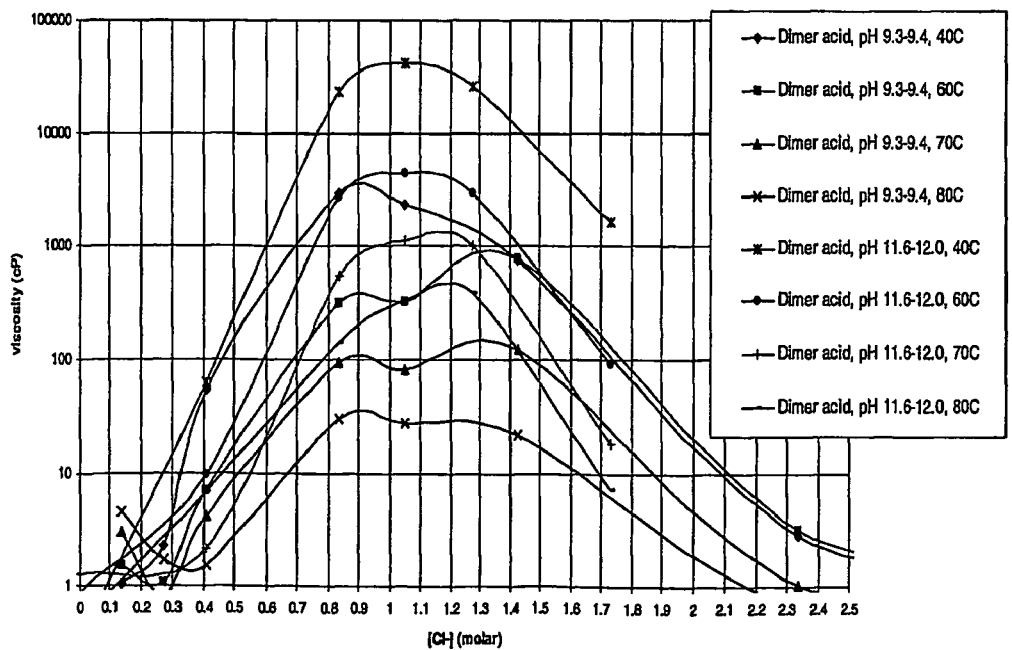
Figure 15:
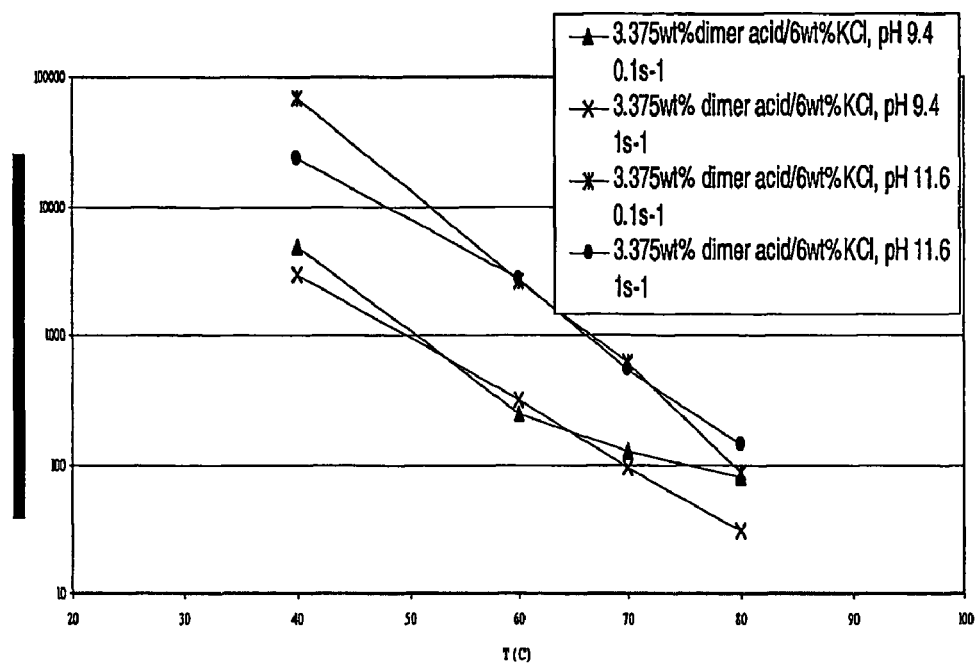
Figure 16:
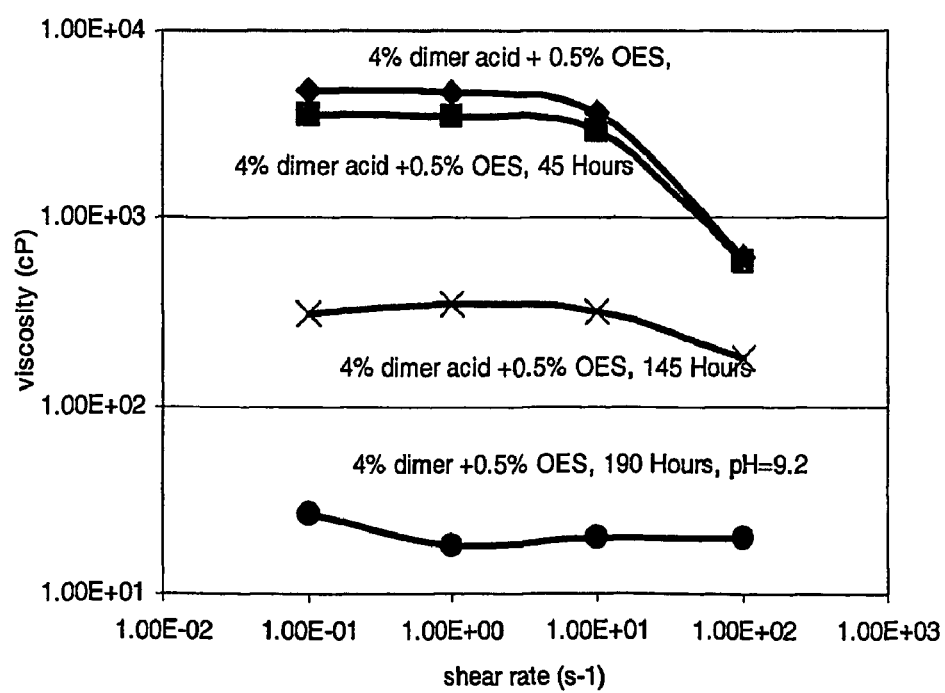
Figure 17:
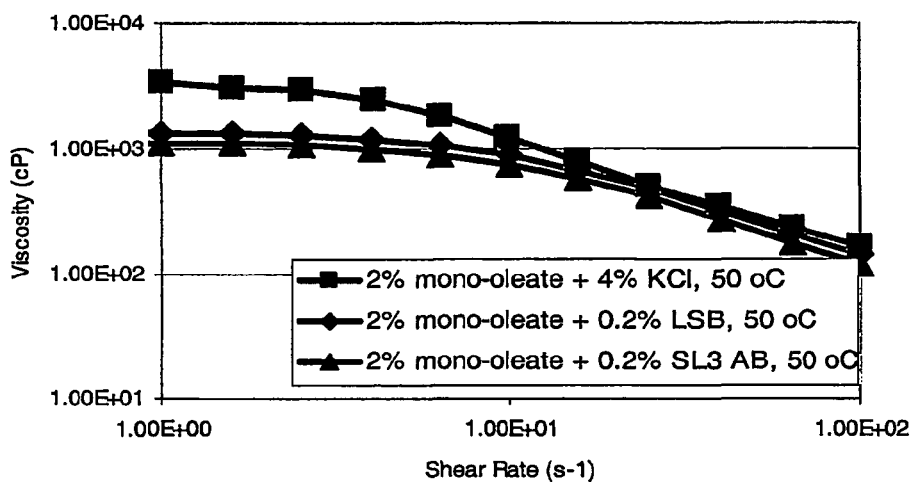
Figure 18:
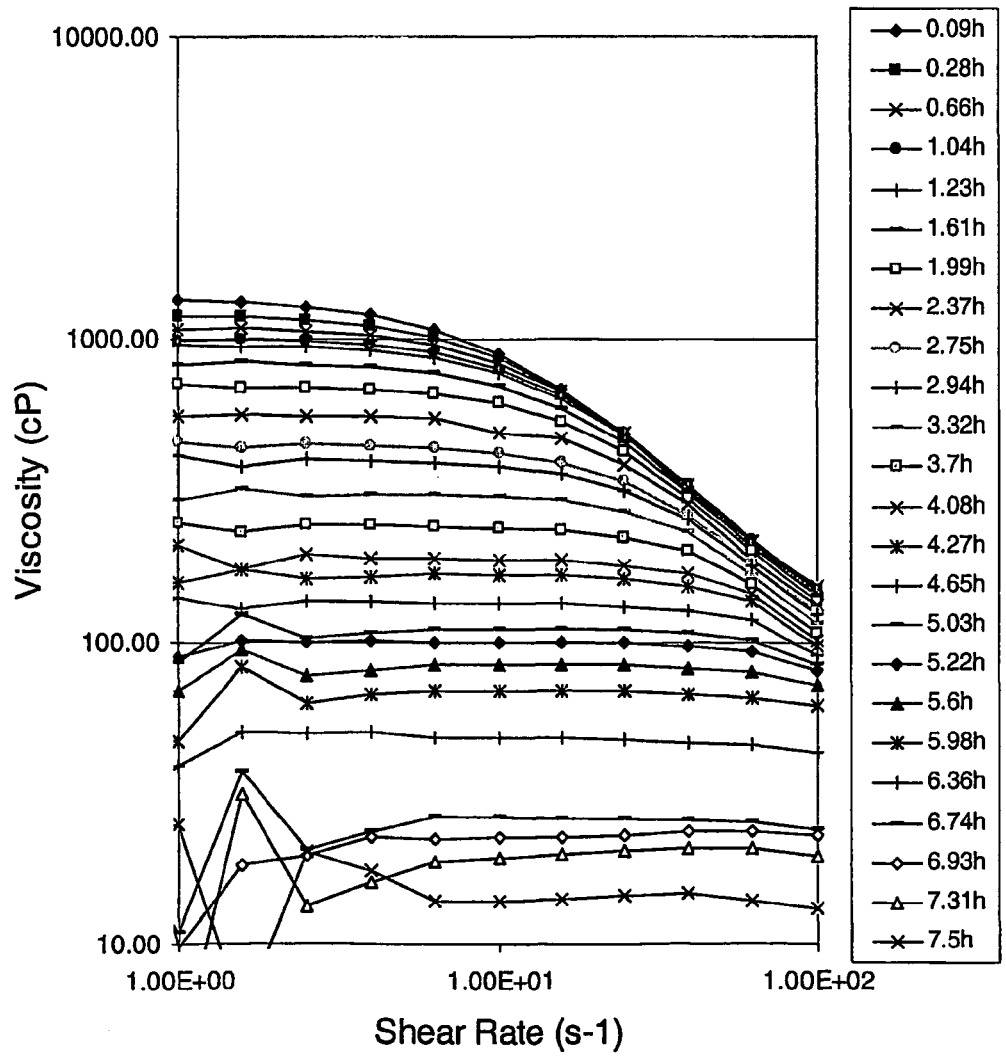
Figure 19:
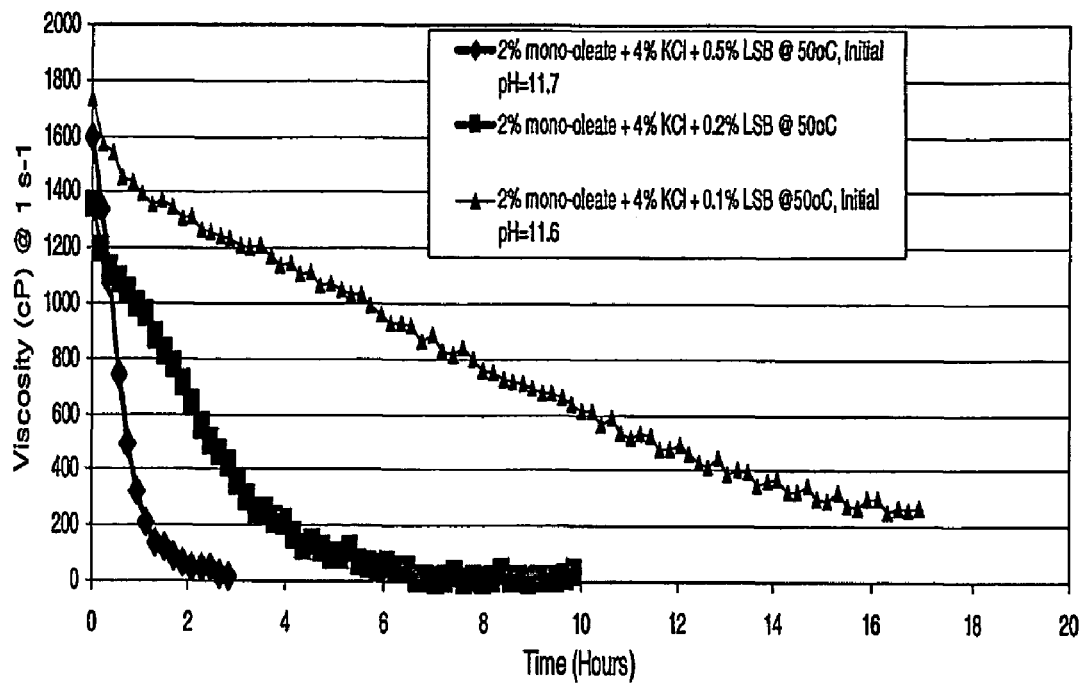
Figure 20:
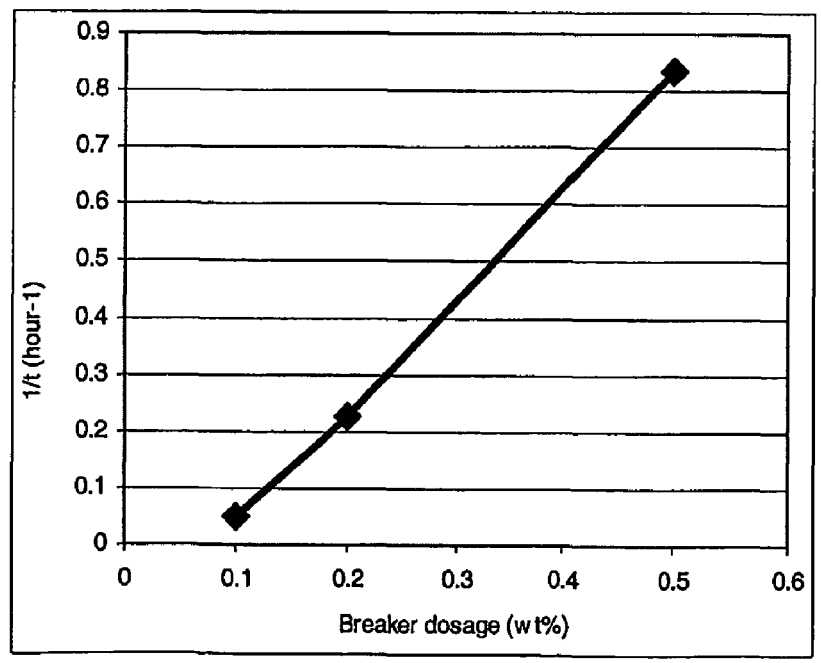
Figure 21:
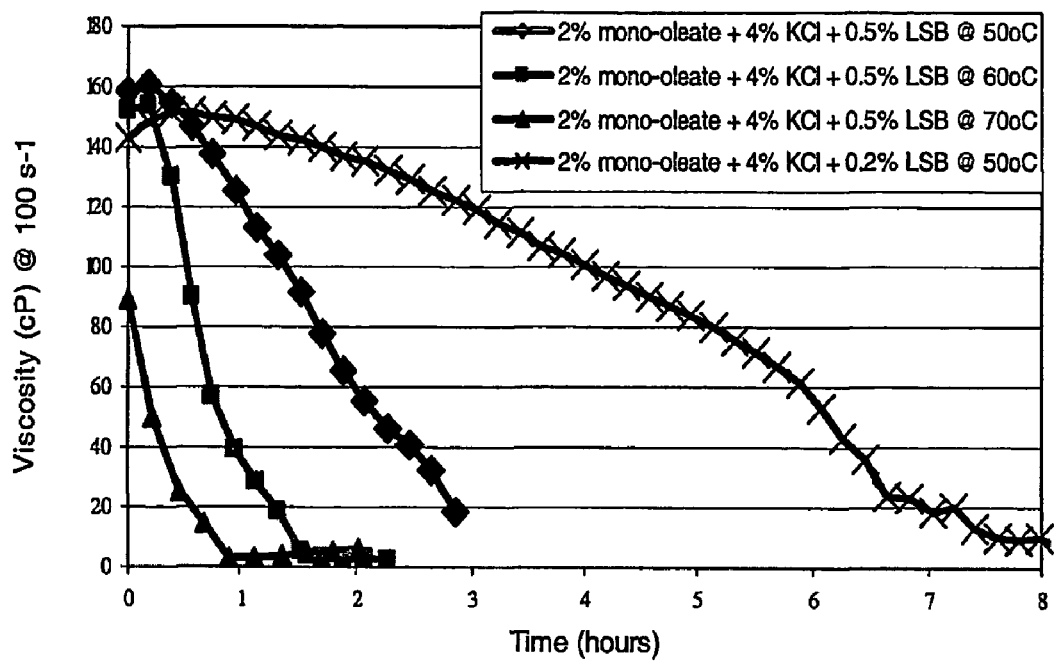
Figure 22:
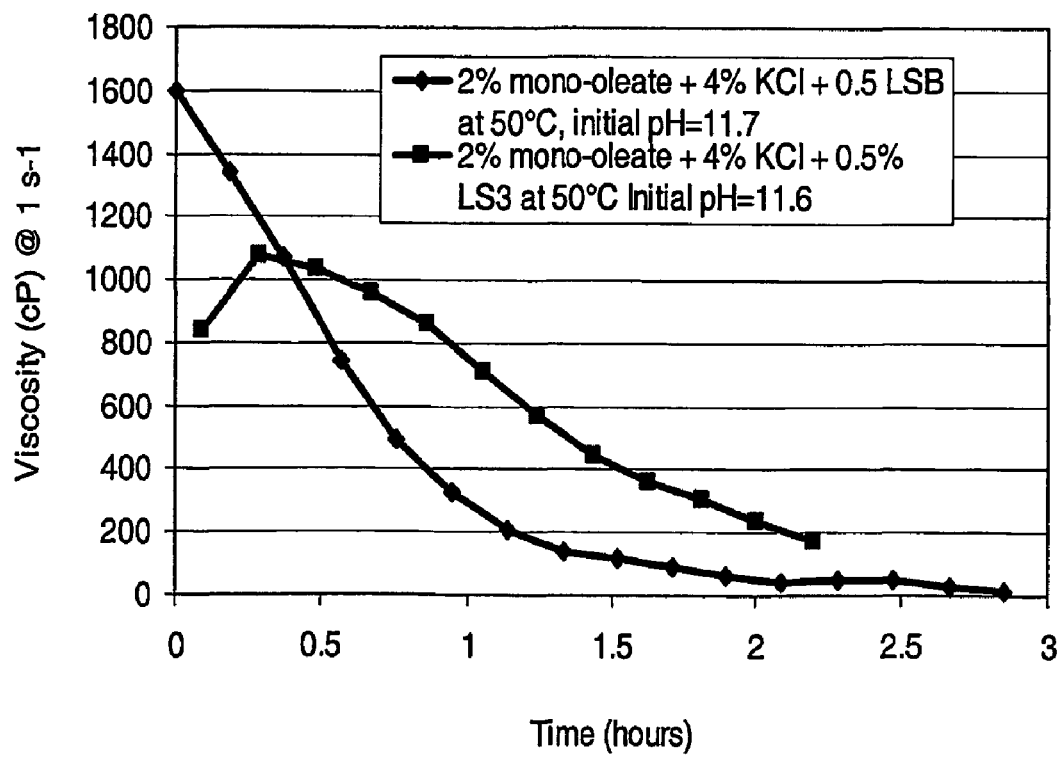

the FIG. 2 shows the breakdown reaction of mono-oleyl succinate;

the FIG. 3 shows the breakdown reaction of disodium laureth sulphosuccinate;

the FIG. 4 shows the breakdown reaction of sodium lauryl sulphoacetate;

the FIG. 5 illustrates the effect alcohols on rheology of N-erucyl-N,N-bis(2-hydroxyethyl)-N-methyl ammonium chloride based gels;

the FIG. 6 illustrates the effect of butanol concentration and temperature on rheology of N-erucyl-N,N-bis(2-hydroxyethyl)-N-methyl ammonium chloride based gels;

the FIG. 7 illustrates the effect of oleyl alcohol on the viscosity of N-erucyl-N,N-bis(2-hydroxyethyl)-N-methyl ammonium chloride based gels;

the FIG. 8 illustrates the impact of the hydrophobicity of esters to the compatibility of N-erucyl-N,N-bis(2-hydroxyethyl)-N-methyl ammonium chloride based gels;

the FIG. 9 illustrates the effect of erucyl ester methylene dimethyl ethyl ammonium chloride on N-erucyl-N,N-bis(2-hydroxyethyl)-N-methyl ammonium chloride based gels;

the FIG. 10 compares the rheology of gels comprising erucyl ester methylene dimethyl ethyl ammonium chloride and N-erucyl-N,N-bis (2-hydroxyethyl)-N-methyl ammonium chloride;

the FIG. 11 illustrates the effect of temperature on the rheology of a gel comprising N-erucyl-N,N-bis(2-hydroxyethyl)-N-methyl ammonium chloride and a diesterquat;

the FIG. 12 illustrates the effect of temperature on the breaking time of a gel comprising N-erucyl-N,N-bis(2-hydroxyethyl)-N-methyl ammonium chloride and a diesterquat;

the FIG. 13 illustrates the effect of oleyl alcohol concentration on the rheology of a gel based on dimer oleic acid;

the FIG. 14 compares the low shear viscosity of gels based on dimeric oleic acid as a function of chloride concentration and fluid pH;

the FIG. 15 compares the low shear viscosity at salt peak of fluids of FIG. 14 as a function of temperature and fluid pH;

the FIG. 16 illustrates the delayed breakdown of viscoelastic surfactant gels based on dimeric oleic acid in the presence of the internal cleavable surfactant breaker mono-oleyl ester succinate;

the FIG. 17 illustrates the effect of a sulphosuccinate/sulphoacetate mixture and sulphosuccinate on flow rheology of a gel system based on dimeric oleic acid;

the FIG. 18 illustrates the delayed breaking of a dimeric oleic acid based viscoelastic gel dosed with a sulphosuccinate/sulphoacetate cleavable surfactant mixture;

the FIG. 19 illustrates the fact that the breaker dosage can be used to control the gel degradation rate;

the FIG. 20 shows the linear relationship that exists between the concentration of active surfactant and the inverse of the time required for a gel to lose 90% of its viscosity at low shear rate;

the FIG. 21 illustrates the effect of temperature on of a dimeric oleic acid based viscoelastic gel comprising a sulphosuccinate/sulphoacetate cleavable surfactant mixture; and the FIG. 22 compares the gel breakdown kinetics for of a dimeric oleic acid based viscoelastic gel dosed with a sulphosuccinate/sulphoacetate mixture or sulphosuccinate cleavable surfactants.

DETAILED DESCRIPTION

The present invention concerns an aqueous fluid for use in the recovery of hydrocarbons such as oil and gas. This aqueous fluid is a wellbore service fluid such as a drilling fluid, a completion fluid, a work over fluid, a packer fluid or a conformance or permeability control fluid and, more particularly, a fracturing fluid.

The fluid of the invention is viscoelastic. Its viscoelasticity may be measured by carrying out dynamic oscillatory rheological measurements as generally described in Barnes H. A. et al., *An Introduction to Rheology*, Elsevier, Amsterdam (1997). In a typical dynamic oscillatory experiment, the fluid is sheared sinusoidally according to the following equation (1):

$$\gamma(t) = \gamma_{(max)} \sin \omega t \qquad (1)$$

where $\gamma(t)$ is the strain, $\gamma(max)$ is the maximum strain, t is time and $\omega$ is the angular frequency. The shear stress, $\sigma$, is given by:

$$\sigma(t) = \sigma_{(max)} \sin(\omega t + \delta) \qquad (2)$$

where $\delta$ is the phase angle.

The relative inputs given by the elastic component (G') and viscous component (G") are resolved as follows. Expanding the sine function in equation (2) gives equations (3) and (4) as follows:

$$\sigma(t) = \sigma_{(max)}[\sin \omega t \cos \delta + \cos \omega t \sin \delta] \qquad (3)$$

$$\sigma(t) = \gamma[G' \sin \omega t + G'' \cos \omega t] \qquad (4)$$

where $G' \equiv (\sigma_{(max)}/\gamma_{(max)}) \cos \delta$ and $G'' \equiv (\sigma_{(max)}/\gamma_{(max)}) \sin \delta$.

Equation (4) therefore defines two dynamic moduli: G', the storage modulus or elastic component and G", the loss modulus or viscous component of a fluid having viscoelastic properties.

The fluid of the present invention is an aqueous viscoelastic gel, where the terms "viscoelastic gel" as used herein mean a composition in which the elastic component (G') is at least as important as the viscous component (G"). In the evolution from a predominantly viscous liquid to a viscoelastic gel, the gel point can be defined by the time when the contribution from the elastic and viscous components becomes equal, i.e. G'=G"; at and beyond this point in time, $G' \geq G''$ and the phase angle, $\delta$ is $\geq 45°$.

The fluid of the invention comprises a first surfactant. This surfactant is said viscoelastic because, unlike numerous surfactants which typically form Newtonian solutions with a viscosity slightly higher than water even at high concentration, it is capable of forming viscoelastic fluids even at lower concentrations. This specific rheological behaviour is mainly due to the types of surfactant aggregates that are present in the fluids. In the fluids with low viscosity, the surfactant molecules, present at a sufficient concentration, aggregate in spherical micelles whereas, in viscoelastic fluids, long micelles, which can be described as worm- or rod-like micelles, are present and entangle.

The first surfactant of the invention is usually ionic. It may be cationic, anionic or zwitterionic depending on the charge of its head group. When the surfactant is cationic, it is associated with a negative counterion which is generally Cl⁻ or an anionic organic species such the salicylate anion. When the surfactant is anionic, it is associated with a positive counterion, generally Na⁺ or K⁺ and, when it is zwitterionic, it is associated with both negative and positive counterions, generally Cl⁻ and Na⁺ or K⁺.

The first surfactant is, for example, of the following formulae:

R—Z where R is the hydrophobic tail of the surfactant, which is a fully or partially saturated, linear or branched hydrocarbon chain of at least 18 carbon atoms and Z is the head group of the surfactant which can be —NR$_1$R$_2$R$_3^+$, —SO$_3^-$, —COO⁻ or, in the case where the surfactant is zwitterionic, —N⁺(R$_1$R$_2$R$_3$—COO⁻) where R$_1$, R$_2$ and R$_3$ are each independently hydrogen or a fully or partially saturated, linear or branched, aliphatic chain of at least one carbon atom, possibly comprising a hydroxyl terminal group.

In another example, the first surfactant is a cleavable viscoelastic surfactant of the following formulae:

R—X—Y—Z where R is the hydrophobic tail of the surfactant, which is a fully or partially saturated, linear or branched hydrocarbon chain of at least 18 carbon atoms, X is the cleavable or degradable group of the surfactant which is an acetal, amide, ether or ester bond, Y is a spacer group which is constituted by a short saturated or partially saturated hydrocarbon chain of n carbon atoms where n is at least equal to 1, preferably 2 and, when n is ≧3, it may be a straight or branched alkyl chain, and Z is the hydrophilic head group of the surfactant which can be —NR$_1$R$_2$R$_3^+$, —SO$_3^-$, —COO⁻ or, in the case where the surfactant is zwitterionic, —N⁺(R$_1$R$_2$R$_3$—COO⁻) where R$_1$, R$_2$ and R$_3$ are each independently hydrogen or a fully or partially saturated, linear or branched, aliphatic chain of at least one carbon atom, possibly comprising a hydroxyl terminal group.

A cationic viscoelastic surfactant suitable for the implementation of the invention is the N-erucyl-N,N-bis(2-hydroxyethyl)-N-methyl ammonium chloride. In an aqueous solution comprising 4 wt % NaCl or 3 wt % KCl, this viscoelastic surfactant forms a gel containing worm-like micelles that entangle at concentrations typically in the range 1–10 wt %. These worm-like micelles degrade to form spherical micelles when the gel is broken by hydrocarbons.

Anionic viscoelastic surfactants suitable for the implementation of the invention are monocarboxylates RCOO⁻ such as oleate where R is C$_{17}$H$_{33}$ or di- or oligomeric carboxylates such as disclosed in the patent application filed on the 11 Jul. 2001 under the number PCT/GB01/03131 not published at the filing date of the present patent application. These mono-, di- or oligomeric carboxylates form viscoelastic gels when in alkaline solution in the presence of added salts such as potassium chloride or sodium chloride. Worm-like micelles of said gel degrade to spherical micelles when the gel is broken by hydrocarbon.

The fluid of the invention comprises a second surfactant. This surfactant is viscoelastic or not. It is said cleavable. As such, it decomposes under downhole conditions to release degradation products. Cleavable surfactants for the implementation of the invention are disclosed in the patent application filed on the 13$^{th}$ February 2001 under the number GB 0103449.5. These surfactants are viscoelastic of the following formulae:

R—X—Y—Z where R is the hydrophobic tail of the surfactant, which is a fully or partially saturated, linear or branched hydrocarbon chain of at least 18 carbon atoms, X is the cleavable or degradable group of the surfactant which is an acetal, amide, ether or ester bond, Y is a spacer group which is constituted by a short saturated or partially saturated hydrocarbon chain of n carbon atoms where n is at least equal to 1, preferably 2 and, when n is ≧3, it may be a straight or branched alkyl chain, and Z is the hydrophilic head group of the surfactant which can be —NR$_1$R$_2$R$_3^+$, —SO$_3^-$, —COO⁻ or, in the case where the surfactant is zwitterionic, —N⁺(R$_1$R$_2$R$_3$—COO⁻) where R$_1$, R$_2$ and R$_3$ are each independently hydrogen or a fully or partially saturated, linear or branched, aliphatic chain of at least one carbon atom, possibly comprising a hydroxyl terminal group.

Typical second surfactants are therefore ester carboxylates, ester sulphonates, for example, where Y=CH$_2$CH$_2$, isethionates, and ester quats. The equivalent reverse and forward amide surfactants, that is to say reverse amide carboxylates, forward amide carboxylates, for example sarcosinates (RCON(CH$_3$)CH$_2$COO⁻), reverse amide sulphonates, forward amide sulphonates, for example taurates (RCON(R')CH$_2$CH$_2$SO$_3^-$), reverse amide quats and forward amide quats are also typical second surfactants according to the invention.

Due to, in particular, the presence of the hydrophilic head group, weight percent concentrations of R—X—Y—Z surfactants are compatible with the viscoelastic surfactant gel even when R is a saturated or partially unsaturated chain with 18 or more carbon atoms.

For example, when X is an ester group, the cleavable surfactant is therefore able to decompose under downhole conditions to release an alcohol breaker according to the following reaction:

ROOC—Y—Z+OH⁻→⁻OOC—Y—X+ROH.

In the same way, the hydrolysis of reverse amide surfactants generates amines which are also an efficient breakers. Also, the hydrolysis of forward ester or forward amide surfactants generates carboxylic acids which can also be efficient gel breakers, in particular when the first surfactant is cationic.

Typically, the alcohol, the amine and the carboxylic acids generated comprise at least 3 carbon atoms. Preferably, they are long chain alcohol, amine or carboxylic acid comprising 8 to 18 carbon atoms or more.

Finally, internal delayed breakers based on cleavable surfactants are advantageously selected according to the invention such that they meet the following performance criteria:

to be present at a concentration enough to generate a sufficient quantity of gel breaker compound, notably a long alcohol, amine or carboxylic acid, without degrading the initial rheological properties of the viscoelastic surfactant gel and, preferably, with enhancing the properties of said viscoelastic surfactant gel; and to degrade, at said concentration, at a controllable rate which is appropriate for a given application. For fracturing application, gel degradation should be controllable in the following range from 1 to 5 hours.

The pH of the viscoelastic gels based on N-erucyl-N,N-bis(2-hydroxyethyl)-N-methyl ammonium chloride may be near neutral when formulated with potassium chloride and mildly acidic when formulated with ammonium chloride. Since the cationic surfactant maintains its positive charge and gelling properties through a broad range of acid, neutral and alkaline conditions, there is scope to use cationic cleavable surfactant breakers in which the cleavable linkage is an ester or amide.

Esterquats are the preferred cleavable surfactant breakers for such gels. Their chemistry, properties and uses are disclosed in Kruger G., Boltersdorf D. and Overkempe K., "*Estequats*", *Novel Surfactants: Preparation, Applications & Biodegrability*, edited by Krister Holmberg, Marcel Dekker, Inc., New York, 1998, pp. 114–138. The general formulae for mono-esterquats is $R-COO-C_n-N(R)_3^+$ for a forward ester and $R-OOC-C_n-N(R)_3^+$ for a reverse ester where, typically, n is 1, 2 or 3 and preferably 2. Usually, they are prepared by reacting a tertiary alkanolamine with a fatty acid, followed by reaction with an alkylating agent to the corresponding quaternary as disclosed in PCT application published under the number WO-91/01295. For example, mono- and di-esterquats may be prepared according to the following reactions:

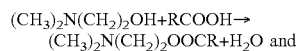
$(CH_3)_2N(CH_2)_2OH+RCOOH \rightarrow$
$(CH_3)_2N(CH_2)_2OOCR+H_2O$ and

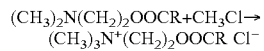
$(CH_3)_2N(CH_2)_2OOCR+CH_3Cl \rightarrow$
$(CH_3)_3N^+(CH_2)_2OOCR\ Cl^-$ and

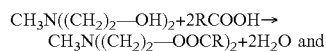
$CH_3N((CH_2)_2-OH)_2+2RCOOH \rightarrow$
$CH_3N((CH_2)_2-OOCR)_2+2H_2O$ and

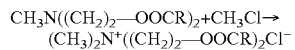
$CH_3N((CH_2)_2-OOCR)_2+CH_3Cl \rightarrow$
$(CH_3)_2N^+((CH_2)_2-OOCR)_2Cl^-$ Less common esterquats are derived from sugar derivatives, wherein the sugar is incorporated via esterification of a carboxylic acid or hydroxyl group. In particular, example of esterquats derived from glucose or sorbitol are described in Kationische Zuckertenside, Seifen Oele Fette Wachse 120:423, 1994. Other examples of esterquats derived from sorbitol are described in the German Patent published under the number 195 39 876. Also, examples of esterquats derived from gluconic acid are given in the German Patent published under the number 195 39 845.

Other esterquats are betaine esters which derive from aminocarboxylic acids and thus have a reverse ester group compared to the forward esterquats based on alkanolamines. Such betaine esters are disclosed in the documents Biermann M., Lange F., Piorr R., Ploog U., Rutzen H., Schindler J. and Schmidt R., *Surfactants in Consumer products*, edited by J. Falbe, Springer-Verlag, Heidelberg (1987), pp. 110–114 and Edebo L., Lindstedt S., Allenmark S. and Thompson R. A., Antimicrob. Agents Chemother. 34:1949 (1990).

Esterquats with two different ester bonds, $R-COO^-$ and $R-OOC$, in the same molecule are disclosed in the application published under the number WO 93/17085. They are prepared by reacting dimethyl ethanolamine with fatty acid and subsequent quaternisation with alkylchloroacetate.

One manufacturer of esterquats is Akzo Nobel™ and the product range of esterquats commercialized by Akzo Nobel™ is marketed under the name Armosoft™. Another manufacturer is Stepan™. This manufacturer markets suitable products under the names AMMONYX GA-90™ and AMMONYX GA-70PG™ which contain the diesterquat shown below:

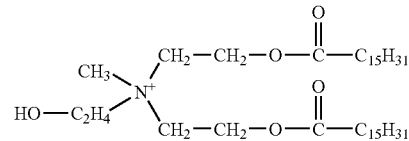

This diesterquat is di(palmitoylethyl) hydroxyethylmethylammonium. The counterion is methosulfphate $CH_3OSO_3^-$. AMMONYX GA-90™ comprises 90 wt % of the diesterquat and 10 wt % of isopropanol whereas the AMMONYX GA-70PG™ comprises 70 wt % of the diesterquat and 30 wt % propylene glycol.

Another esterquat suitable for the implementation of the invention is erucyl ester methylene dimethyl ethyl ammonium chloride shown in the following formula:

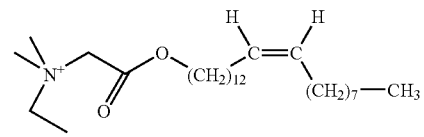

Figure 1:
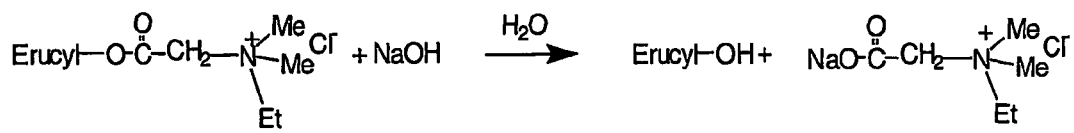

Under certain conditions, the reverse ester bond of this esterquat cleaves resulting in the generation of erucyl alcohol according to the breakdown reaction shown in FIG. 1. Erucyl alcohol is an efficient breaker of aqueous viscoelastic fluids of the invention.

Viscoelastic gels comprising oleate surfactants require an alkaline condition with a pH equal or greater than about 11. Given this constraint, candidate internal delayed breakers are a broad range of anionic cleavable surfactants including: —esters, amides or ether carboxylates; —ether sulphonates; —ether sulphates; and —phosphate esters. Their suitability however depends on their ability to deliver the appropriate degradation kinetics starting from an initial pH equal or greater than about 11.

A cleavable surfactant suitable for the oleate surfactant viscoelastic gels is the mono-oleyl ester succinate. It is an anionic cleavable surfactant comprising a cleavable ester bond between the oleyl hydrophobic and the carboxylate hydrophilic group. Under alkaline conditions, it cleaves to release oleyl alcohol and the succinate anion. The corresponding reaction is shown in the FIG. 2.

Other cleavable surfactants may however be suitable for breaking oleate surfactant gels or dimer/trimer carboxylate gels. These are based on sulphosuccinate and sulphoacetate surfactants.

For example, alkyl sulphosuccinates are mono- or di-esters of sulphosuccinic acid $HOOCCH_2-CH(SO_3H)COOH$. The formulae of these mono- and di-esters of sulphosuccinic acid are as follows:

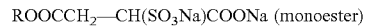
$ROOCCH_2-CH(SO_3Na)COONa$ (monoester)

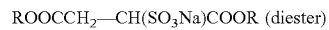
$ROOCCH_2-CH(SO_3Na)COOR$ (diester)

where R is an alkyl chain.

Two different second surfactants suitable for the implementation of the invention are available from the Stepan™ Company. The first is disodium laureth sulphosuccinate:

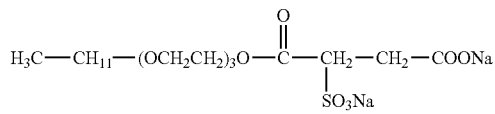

The second is a sulphoacetate surfactant, sodium lauryl sulphoacetate:

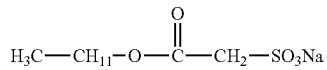

STEPAN-MILD LSB™ is a liquid product containing both the disodium laureth sulphosuccinate and sodium lauryl sulphoacetate surfactants in water, the total surfactant activity being 25 wt %. This surfactant tolerates hard water and it is readily biodegradable. The recommended temperature for storage is between 7° C. and 43° C. STEPHAN-MILD SL3™ is also a liquid containing 30 wt % disodium laureth sulphosuccinate. Both surfactants can decompose to release long chain alcohols as illustrated in the FIGS. 3 and 4. This decomposition is accompanied by a decrease in fluid pH due to the consumption of the ion OH$^-$. In addition, the presence of the sulphonate group accelerates the rate of ester hydrolysis such that ROOCCH$_2$—CH(SO$_3$Na)COONa degrades more rapidly than its non-sulphonated equivalent ROOCCH$_2$—CH$_2$COONa and ROOCCH$_2$—SO$_3$Na will degrade more rapidly than ROOCCH$_3$. In both cases, the presence of the sulphonate group increases the hydrophilicity and water solubility of the compound and this enhances compatibility with the gel.

In addition to the first and second surfactants, the aqueous fluid of the invention may comprise salts including, for example, inorganic salts such as ammonium, sodium or potassium chlorides present in concentrations of 1 to 10 wt % and, typically, 3 to 4 wt %, or organic salts such as sodium salicylate. The fluid may also comprise an organic solvent such as isopropanol, which increases the liquefaction of the surfactant molecules.

Practically, all compounds of the fluid of the invention are blended at surface together with the propping agent, which can be, for example, a 20–40 mesh sand, bauxite or glass beads. When subjected to a very high shear rate, the viscosity of the fluid is sufficiently low to allow its pumping downhole. There, the pumped fluid is injected into the formation rocks to be fractured under a high pressure. At that time, the fluid of the invention is sufficiently viscous for carrying the propping agent through the fracture. At a given time after fracturing per se, the second surfactant decomposes to release a compound that will break the gel. This appears particularly advantageous when the produced hydrocarbons flowing back the fractures is substantially free of significant quantity of hydrocarbon in a liquid phase.

EXAMPLE 1

Effect of Alcohols on the Fluid Rheology

On FIG. 5 is plotted the viscosity of a gel comprising 3 wt % N-erucyl-N,N-bis(2-hydroxyethyl)-N-methyl ammonium chloride, 1 wt % isopropanol and 3 wt % NH$_4$Cl and that of equivalent gels which also contain 1 wt % methanol, ethanol, n-propanol, isopropanol, n-butanol or n-pentanol, as a function of shear rate, at 60° C. The presence of a low concentration of alcohol reduces the viscosity of the viscoelastic surfactant gel. In particular, the viscosity is reduced at a shear rate below 10 s$^{-1}$. The gel breaking efficiency increases with the number of carbon atoms in the alcohol and so, with the hydrophobicity of said alcohol.

On FIG. 6 is plotted the viscosity of an aqueous gel comprising 3 wt % of a fluid (cationic VES) comprising 75 wt % N-erucyl-N,N-bis(2-hydroxyethyl)-N-methyl ammonium chloride and 25 wt % isopropanol, 3 wt % NH$_4$Cl and 0, 0.5, 1 or 1.5 wt % butanol, as a function of shear rate, either at 25 or at 60° C. As shown in this figure, the gel breaking efficiency of alcohols also increases with the alcohol concentration and with temperature.

On FIG. 7 is plotted the viscosity of an aqueous gel comprising 2 wt % of a fluid comprising 60.5 wt % N-erucyl-N,N-bis(2-hydroxyethyl)-N-methyl ammonium chloride, isopropanol and ethylene glycol, 3 wt % KCl and oleyl alcohol, as a function of the oleyl alcohol concentration, at room temperature, under a low shear rate of . . . s$^{-1}$. As shown in this figure, the addition of oleyl alcohol causes a dramatic decrease in the low shear viscosity of the gel which increases with its concentration.

EXAMPLE 2

Relationship Between the Hydrophobicity of Esters and Compatibility with the Fluid On FIG. 8 is plotted the viscosity of an aqueous gel containing 4.5 wt % surfactant (comprising 75 wt % N-erucyl-N,N-bis(2-hydroxyethyl)-N-methyl ammonium chloride and 25 wt % isopropanol), 0.75 wt % hydrophobically-modified polyacrylamide, 3 wt % NH$_4$Cl and a dimethyl dibasic ester which can be dimethyl itaconate, dimethyl malonate, dimethyl malate, dimethyl oxalate, dimethyl glutarate, dimethyl adipate, dimethyl malonate or dimethyl azelate, as a function of the dibasic ester concentration, at 25° C. The more hydrophilic dibasic esters, for example dimethyl itaconate, dimethyl malate and dimethyl oxalate are compatible with the gel even when present at 3–4 wt %.

The alkaline hydrolysis of dibasic esters is described by the following reaction:

where R$_2$ are alkyl groups and Y is a link group in the dibasic ester.

In the present example, R$_2$ is CH$_3$ and Y depends on the particular dibasic ester chosen. It appears that, as the number of carbon atoms increases in Y and so, as the hydrophobicity of the dibasic ester increases, its compatibility with the viscoelastic surfactant gel is reduced. The gel compatibility limit determined from the FIG. 8 is given by the addition of about 1 wt % of dimethyl glutarate, which can decompose to generate 0.4 wt % methanol.

This relationship between the hydrophobicity of esters and compatibility with the fluid would have been the same for classical monobasic esters which hydrolyses under alkaline conditions according to the following reaction:

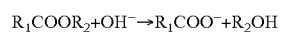

where R$_1$ is also an alkyl group.

EXAMPLE 3

Aqueous Viscoelastic Fluid Wherein the Second Surfactant is Erucyl Ester Methylene Dimethyl Ethyl Ammonium Chloride On FIG. 9 is plotted the viscosity of aqueous gels comprising 2 wt % of a fluid (cationic surfactant) comprising 60.5 wt % N-erucyl-N,N-bis(2-hydroxyethyl)-N-methyl ammonium chloride, isopropanol and ethylene glycol, 4 wt % KCl and 0 or 0.5 wt % erucyl ester methylene dimethyl ethyl ammonium chloride as a function of shear rate, at room temperature.

It appears that erucyl ester methylene dimethyl ethyl ammonium chloride is compatible with a typical the N-erucyl-N,N-bis(2-hydroxyethyl)-N-methyl ammonium chloride fluid. Its presence even actually enhances the initial viscosity of the gel.

The degradation kinetics of the above gel comprising 0.5 wt % erucyl ester methylene dimethyl ethyl ammonium chloride was then studied for various pH and at 25, 45 or 60° C. Table 1 below illustrates the results that were obtained:

TABLE 1

| T (° C.) | Initial pH | pH control | Degradation Time (hours) [Time to <1000 cP at 1 s$^{-1}$] | Degradation Time (hours) [Time to <50 cP at 100 s$^{-1}$] |
|---|---|---|---|---|
| 25 | 6.32 | 0.5 wt % NH$_4$ acetate | 7.5 | 20 |
| 25 | 8.46 | 0.1% K bicarbonate | 3 | 3 |
| 45 | 5.17 | 0.5 wt % K acetate + CH$_3$COOH | >12 | 16 |
| 45 | 6.32 | 0.5 wt % NH$_4$ acetate | 2.5 | 9 |
| 60 | 7.99 | 0.1 wt % K acetate | 1 | 1 |
| 60 | 7.47 | 0.5 wt % K formate | 2.8 | 2.8 |
| 60 | 7 | No buffer (evolves to acid pH) | 7.5 | 7.5 |
| 60 | 6.32 | 0.5 wt % NH$_4$ acetate | 0.8 | 1.2 |
| 60 | 7 | No buffer* (evolves to acid pH) | 3 | 3 |

*in place of erucyl ester methylene dimethyl ethyl ammonium chloride, 0.5 wt % of an equivalent cleavable surfactant with a saturated hydrophobic tail group comprising 22 carbon atoms was used.

By varying the initial pH of the fluid using simple buffer additives, it is possible to delay the gel breaking process from 1 to 24 hours. A longer delay is achieved when a more acidic conditions is used. Near-neutral or mildly alkaline condition is appropriate for low temperature treatments comprised between 25 and 45° C. Near-neutral or mildly acidic condition is appropriate for higher temperature range comprised between 45 and 60° C.

On FIG. 10 is plotted the viscosity of aqueous gels comprising 2 wt % of a fluid (cationic surfactant) comprising 60.5 N-erucyl-N,N-bis(2-hydroxyethyl)-N-methyl ammonium chloride, isopropanol and ethylene glycol, 4 wt % KCl and 0.5 wt % erucyl ester methylene dimethyl ethyl ammonium chloride as a function of shear rate, for different times, at 60° C. In an initial phase from 0 to 70 minutes, the partial breakdown of erucyl ester methylene dimethyl ethyl ammonium chloride results in an increase in the low shear viscosity of the gel. During this period, erucyl alcohol appears to act as a co-surfactant which modifies the micelle structure such that the gel strength increases. This initial phase is followed by a progressive decrease in both the low and high shear viscosity to the point that the fully degraded fluid has a near-Newtonian viscosity around 8 cP.

EXAMPLE 4

Aqueous Viscoelastic Fluid Wherein the Second Surfactant is AMMONYX GA-90™

On FIG. 11 is plotted the viscosity of aqueous gels comprising 4 wt % of a fluid (cationic surfactant) comprising 60.5 wt % N-erucyl-N,N-bis(2-hydroxyethyl)-N-methyl ammonium chloride, isopropanol and ethylene glycol, 4 wt % KCl and 0 or 0.1 wt % AMMONYX GA-90™ under a shear of 1 or 100 s$^{-1}$, as a function of temperature and at pH equal to 6.3. AMMONYX GA-90™ is reasonably compatible with the gel. In the presence of 0.1 wt % of AMMONYX GA-90™, the gel has a lower viscosity in the temperature range up to 160° F. (71° C.) but a higher viscosity in the range 176–194° F. (80–90° C.). At high temperatures however, AMMONYX GA-90™ decomposes to the more hydrophilic tri(hydroxyethyl)methylamonium ion and palmitic acid. At the same time, the fluid pH evolves from 6.3 to around 3 and, under this acidic condition, palmitic acid is a hydrophobic species which efficiently breaks the gel.

On FIG. 12 is plotted the viscosity of the above gel comprising 0.1 wt % AMMONYX GA-90™ as a function of time, when the formulation is aged at 60 and 70° C. It is observed that the time to a viscosity <1000 cP (at 1 s$^{-1}$) decreases from 15 to 5 hours when the temperature is increased from 60 to 70° C.

EXAMPLE 5

Aqueous Viscoelastic Fluid Wherein the First Surfactant is a Dimeric Oleic Acid On FIG. 13 is plotted the viscosity of aqueous fluids comprising 4 wt % dimeric oleic acid, 6 wt % KCl and 0, 0.05, 0.1, 0.2 or 0.5 wt % oleyl alcohol, at 60° C. and for a pH equal to 13. The dimeric oleic acid used in the present example and in example 6 is coded U1009 by Unichema International, Bebington, Wirral, Merseyside, United Kingdom. At a high pH, this dimeric acid is converted to carboxylate anions. In the FIG. 13, it appears that increasing concentrations of oleyl alcohol facilitate the breaking of the fluid. However, by comparison with the data shown in the FIG. 7, it appears that the present gel has a higher tolerance to the presence of oleyl alcohol such that more than 0.5 wt % of oleyl alcohol is required to fully break said gel at 60° C.

Other experiments have been made which show that the viscoelastic properties of gels based on potassium oleate, monomer, dimer or trimer, are highly sensitive to fluid pH. Typically, when the pH of the fluid is less than 11, the gel is weak and its viscosity is lost at a pH $\leq 10.5$. This behaviour offers another route in terms of the design of a delayed internal breaker which can slowly degrades to reduce the fluid pH.

EXAMPLE 6

Aqueous Viscoelastic Fluid Wherein the Second Surfactant is Mono-Oleyl Ester Succinate On FIG. 14 is plotted the low shear viscosity of aqueous fluids comprising 3.375 wt % of dimeric oleic acid as a function of chloride concentration added as KCl and fluid pH, at 40, 60, 70 or 80° C. The viscosity of the fluids appears to be maximal at a given chloride concentration comprised between 0.9 and 1.2 molar.

On FIG. 15 is plotted the viscosity at salt peak of a fluid comprising 3.375 wt % of dimeric oleic acid, 6 wt % KCl as a function of the temperature, for a pH equal to 9.4 or 11.6, under a shear rate of 0.1 or 1 $s^{-1}$. A decrease in fluid pH results in a considerable decrease in the gel strength and viscosity of salt-optimised gels based on the dimeric oleic acid.

On FIG. 16 is plotted the viscosity of aqueous fluids comprising 4 wt % dimeric oleic acid, 6 wt % KCl and 0.5 wt % oleyl ester succinate as a function of shear rate, at 0, 45, 145 or 190 hours, for an initial pH of 11.5 and at 60° C. The rheology of the formulation evolves from a viscoelastic gel with low shear viscosity between 4800 and 4600 cP and a high shear viscosity between 588 cP to a low viscosity solution with near-Newtonian viscosity around 20 cP.

When used as an internal delayed breaker for an oleate viscoelastic surfactant system, both the release of oleyl alcohol and the concomitant decrease in fluid pH serve to break the oleate gel. The efficiency with which the mono-oleyl succinate breaker can reduce the pH of the oleate gel depends on its initial concentration and the initial pH of the formulation. When added at an initial concentration of 0.5 wt %, the cleavable surfactant can reduce the pH of a typical oleate fluid from 11.5 to 9.2. If the initial pH is greater than 12 and so, if the initial concentration of hydroxide is similar to or higher than the initial concentration of mono-oleyl succinate, then the gel is broken down too rapidly for the application. This rapid gel degradation can be almost instantaneous even at ambient surface temperature. Therefore, according to the invention, the initial pH condition is advantageously controlled.

EXAMPLE 7

Aqueous Viscoelastic Fluid Wherein the Second Surfactants are Sulphosuccinates or Sulphoacetates FIG. 17 compares the viscosity of aqueous fluids comprising 2 wt % mono-oleic acid, 4 wt % KCl with such fluids further comprising 0.2 wt % active cleavable surfactant added in the form of STEPAN-MILD LSB™ or STEPAN-MILD SL3™, as a function of shear rate, at 50° C. At a high pH, mono-oleic acid is converted to mono-oleate. The cleavable surfactants contained in STEPAN-MILD LSB™ and STEPAN-MILD SL3™ appear to be compatible with the dimeric oleic acid viscoelastic surfactant gel. However, the compatibility of STEPAN-MILD LSB™, containing both the sulphosuccinate and sulphoacetate surfactants, is greater than the compatibility of STEPAN-MILD SL3™ containing only the sulphosuccinate surfactant. Also, both surfactants induce a significant decrease in the low and high shear viscosity of the aqueous fluid.

FIG. 18 compares the viscosity of aqueous fluids comprising 2% wt mono-oleic acid, 4 wt % KCl and 0.2 wt % active cleavable surfactant added as STEPAN-MILD LSB™ as a function of shear rate, for various times when the fluid is aged at a constant temperature of 50° C. The initial pH is 11.7 and the final pH, at 7.5 h, is 9.7. A systematic decrease in the low and high shear rate viscosity is observed during the 7.5 hour ageing period. After 7.5 hours, the gel has been degraded to a fluid with near-Newtonian viscosity of about 20 cP.

On FIG. 19 is plotted the viscosity of aqueous fluids comprising 2 wt % mono-oleic acid, 4 wt % KCl and 0.1, 0.2 or 0.5 wt % active cleavable surfactant STEPAN-MILD LSB™ as a function of time, at 50° C. The dosage of cleavable surfactant breaker affects the rate at which the low shear viscosity of the gel degrades. The data indicate that the range of gel degradation kinetics is appropriate for the application and for a given initial pH condition, the breaker dosage can be used to control the rate.

A simpler way to describe the relationship between breaker dosage and gel breakdown rate is shown in FIG. 20 where the x-axis is the concentration of active surfactant added as STEPAN-MILD LSB™ and the y-axis is 1/t, where t is the time required for the gel to lose 90% of its original viscosity at 1 $s^{-1}$. The linear relationship shown in FIG. 20 is valid for the constant ageing temperature 50° C.

On FIG. 21 is plotted the viscosity at a shear rate of 100 $s^{-1}$ of a gel comprising 2 wt % mono-oleic acid, 4 wt % KCl and 0.5 wt % or 0.2 wt % active STEPAN-MILD LSB™, as a function of time, for the following temperatures: 50, 60, 70° C. At 50° C., the gel containing 0.5 wt % STEPAN-MILD LSB™ is broken in about 3 hours. At 60° C. it is broken in about 1.5 hour and at 70° C., it is broken in about 1 hour.

FIG. 22 compares the delayed breaker performance of the two STEPAN-MILD LSB™ and STEPAN-MILD LS3™. The comparison is made at a constant active surfactant concentration of 0.5 wt % using the same gel formulation and initial pH aged at 50° C. The initial viscosity of the system with STEPAN LS3™, is significantly lower than that of the system with STEPAN LSB™. The fluid comprising STEPAN-MILD LS3™ may degrade faster than that the fluid comprising STEPAN-MILD LSB™. The data also suggest that a more efficient cleavable breaker system for mono-oleic acid may be given by the use of a product containing only lauryl sulphoacetate.

The invention claimed is:

1. Aqueous viscoelastic fluid for use in the recovery of hydrocarbons, comprising:
    a first surfactant, said surfactant being viscoelastic;
    a second surfactant, said second surfactant being able to decompose under downhole conditions to release a compound, said compound being able to reduce the viscosity of the aqueous viscoelastic fluid.

2. The fluid of claim 1 wherein the first surfactant is of the following formulae:

R—Z where R is the hydrophobic tail of the surfactant, which is a fully or partially saturated, linear or branched hydrocarbon chain of at least 18 carbon atoms and Z is the head group of the surfactant which is $-NR_1R_2R_3^+$, $-SO_3^-$, $-COO^-$ or, in the case where the surfactant is zwitterionic, $-N^+(R_1R_2R_3-COO^-)$ where $R_1$, $R_2$ and $R_3$ are each independently hydrogen or a fully or partially saturated, linear or branched, aliphatic chain of at least one carbon atom, possibly comprising a hydroxyl terminal group.

3. The fluid of claim 1 wherein the first surfactant is cleavable.

4. The fluid of claim 1 wherein the first viscoelastic surfactant is N-erucyl-N,N-bis(2-hydroxyethyl)-N-methyl ammonium chloride.

5. The fluid of claim 1 wherein the first surfactant is a mono-, di- or oligomeric carboxylate.

6. The fluid of claim 5 wherein the first surfactant is oleate.

7. The fluid of claim 1 wherein the second surfactant is a viscoelastic surfactant.

8. The fluid of claim 1 wherein the second surfactant is of the following formulae:

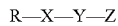

where R is the hydrophobic tail of the surfactant, which is a fully or partially saturated, linear or branched hydrocarbon chain of at least 18 carbon atoms, X is the cleavable or degradable group of the surfactant which is an acetal, amide, ether or ester bond, Y is a spacer group which is constituted by a short saturated or partially saturated hydrocarbon chain of n carbon atoms where n is at least equal to 1, preferably 2 and, when n is $\geq 3$, it may be a straight or branched alkyl chain, and Z is the hydrophilic head group of the surfactant which is $-NR_1R_2R_3^+$, $-SO_3^-$, $-COO^-$ or, in the case where the surfactant is zwitterionic, $-N^+(R_1R_2R_3-COO^-)$ where $R_1$, $R_2$ and $R_3$ are each independently hydrogen or a fully or partially saturated, linear or branched, aliphatic chain of at least one carbon atom, possibly comprising a hydroxyl terminal group.

9. The fluid of claim 8 wherein the second surfactant is an ester carboxylate, an ester sulphonate, an esterquat, a reverse amide carboxylate, a forward amide carboxylate, a reverse amide sulphonate, a forward amide sulphonate, a reverse amide quat or a forward amide quat.

10. The fluid of claim 9 wherein the second surfactant is a mono- or a diesterquat.

11. The fluid of claim 10 wherein the esterquat is a betaine ester.

12. The fluid of claim 10 wherein the esterquat is di(palmitoylethyl) hydroxyethylmethylammonium or erucyl ester methylene dimethyl ethyl ammonium.

13. The fluid of claim 9 wherein the second surfactant is mono-oleyl ester succinate.

14. The fluid of claim 9 wherein the second surfactant is a sulphosuccinate or a sulphoacetate surfactant.

15. The fluid of claim 14 wherein the second surfactant is disodium laureth sulphosuccinate or sodium lauryl sulphoacetate.

16. The fluid of claim 1 wherein the compound is an alcohol, an amine or a carboxylic acid.

17. The fluid of claim 16 wherein the alcohol, the amine or the carboxylic acid comprise an alkyl chain of at least 3 carbon atoms.

18. The fluid of claim 16 wherein the alcohol, amine or carboxylic acid are long chain alcohol, amine or carboxylic acid comprising 8 to 18 carbon atoms or more.

19. The fluid of claim 16 wherein the alcohol is oleyl alcohol.

20. Method for use in the recovery of hydrocarbons comprising the following steps:
   providing an aqueous viscoelastic fluid comprising a first surfactant, said first surfactant being viscoelastic, and a second surfactant able to decompose under downhole conditions;
   allowing said second surfactant to decompose under downhole conditions to release a compound able to reduce the viscosity of the aqueous viscoelastic fluid; and
   allowing the viscosity of the fluid to be reduced downhole.

21. Method of claim 20 wherein the compound released reduces the pH of the viscoelastic fluid, said reduction of pH facilitating the reduction of the viscosity of said fluid.

* * * * *